US00PP29957P2

(12) United States Plant Patent
Hansen

(10) Patent No.: US PP29,957 P2
(45) Date of Patent: Dec. 4, 2018

(54) ***SALVIA* PLANT NAMED 'BALLERINA PINK'**

(50) Latin Name: *Salvia pratensis*
Varietal Denomination: Ballerina Pink

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/732,698

(22) Filed: Dec. 15, 2017

(51) Int. Cl.
*A01H 5/02* (2018.01)

(52) U.S. Cl.
USPC ..... Plt./475

(58) Field of Classification Search
USPC ..... Plt./475
See application file for complete search history.

*Primary Examiner* — Annette H Para

(57) ABSTRACT

The new and distinct cultivar of perennial *Salvia* plant named 'Ballerina Pink' characterized by its very large light pink flowers from purplish red buds, densely arranged in verticils. The new plant has a compact habit with stiff, upright, heavily-branched stems showing slight greyed-purple tinting and persistent calyxes of similar greyed-purplish red tinting, a strong vigorous growth rate and gray-green foliage.

1 Drawing Sheet

Botanical denomination: *Salvia pratensis.*
Cultivar designation: 'Ballerina Pink'.

BACKGROUND OF THE INVENTION

The present invention relates to a new and distinct cultivar of ornamental sage plant hereinafter referred to by the cultivar name *Salvia* 'Ballerina Pink' or as the new plant. The new plant was selected as a single seedling from an open pollination in late spring of 2013 with 'Pink Dawn' U.S. Plant Pat. No. 26,343 as the female or seed parent and the male parent is unknown but may have been any sage from a large number of other hybrids within the breeding area of a wholesale perennial nursery in Zeeland, Mich., USA. The new plant was initially evaluated in the summer of 2014 and assigned the breeder code 13-10-3 through the trial process.

The new *Salvia* was further evaluated and asexually propagated by basal cuttings taken at the same nursery in Zeeland, Mich., USA in 2015. Evaluation of these and further cutting grown plants shows that *Salvia* 'Ballerina Pink' continues to be stable and produce true to type plants in successive generations of asexual propagation.

No plants of *Salvia* 'Ballerina Pink' have been sold or disclosed in this country or anywhere in the world, prior to the filing of this application, nor has any disclosure of the new plant been made prior to the filing of this application with the exception of that which may have been disclosed within one year of the filing of this application and was either derived directly or indirectly from the inventor.

SUMMARY OF THE INVENTION

Plants of *Salvia* 'Ballerina Pink' have not been observed under all possible environmental conditions. The phenotype may vary somewhat with variations in environment such as temperature, nutrition and light intensity without, however, any variance in genotype.

*Salvia* 'Ballerina Pink' can be closely compared with *Salvia* 'Sweet 16' U.S. Plant Pat. No. 24,312, *Salvia* 'Pink Dawn' U.S. Plant Pat. No. 26,343 and *Salvia* 'Pretty in Pink' U.S. Plant Pat. No. 29,550.

*Salvia* 'Ballerina Pink' can also be compared with *Salvia*, 'Pink Friesland' U.S. Plant Pat. No. 18,152 and *Salvia* 'Eveline' U.S. Plant Pat. No. 14,905. Compared with *Salvia* 'Eveline' the flowers of the new plant are larger. The stems and calyxes of 'Pink Dawn' are much darker pigmented with greyed-purple than the new plant, the flowers are darker, deep, purplish pink and the habit is smaller than the new plant. 'Pink Friesland' has a shorter less upright habit with smaller flowers of a stronger purplish red than the new plant. The new plant can also be compared to *Salvia* 'Endless Love' U.S. Plant Pat. No. 21,707 which has a *Salvia verticillata* background and flowers on whorled scapes that are more purple and less pink and smaller in size than the new plant.

The following characteristics in combination distinguish *Saliva* 'Ballerina Pink' as a new and distinct cultivar from all other cultivars known to the inventor:

1. Very large light pink flowers densely arranged in verticils;
2. Stiff, upright, heavily-branched medium green stems with greyed-purple tinting in high light;
3. Calyces in high light developing greyish purplish red;
4. Strong purplish-red flower buds;
5. Compact, rounded, strong, vigorous and winter-hardy habit;
6. Rugose gray-green foliage.

BRIEF DESCRIPTION OF THE DRAWINGS

The photographs of the new plant demonstrate the unique traits and the overall appearance of *Salvia* 'Ballerina Pink'. The colors are as accurate as reasonably possible with color reproductions. Variation in ambient light spectrum, source and direction may cause the appearance of minor variation in color. The plant used in the photographs was a two-year-old plant grown in an open, full-sun trial area at a wholesale perennial nursery in Zeeland, Mich. with supplemental water and fertilizer when needed. Plant growth regulators have been used in greenhouse grown trials only.

DETAILED BOTANICAL DESCRIPTION

Figure 1:
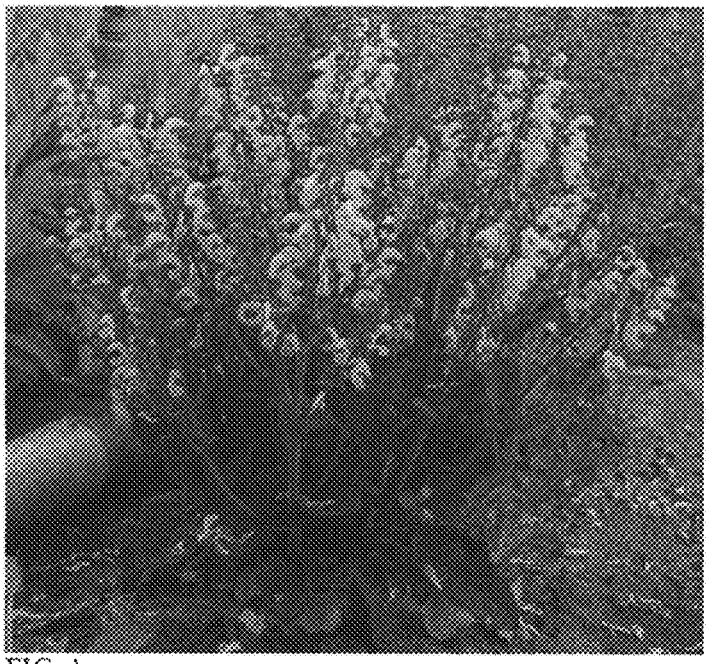
FIG. 1 shows the plant habit in full flower in a full-sun trial area.
Figure 2:
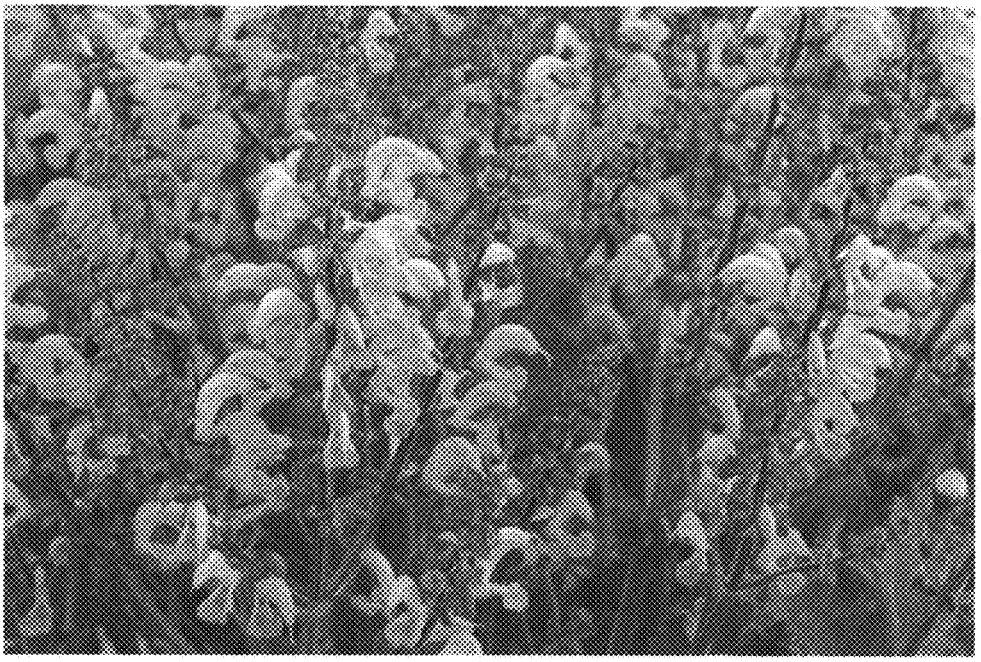
FIG. 2 shows a close-up of the flower scape with the buds, flowers, stems and calyxes.

The following descriptions and color references except where common dictionary terms are used are based on the 2015 edition of The Royal Horticultural Society Colour Chart. *Salvia* 'Ballerina Pink' has not been observed under all possible environments. The phenotype may vary slightly with different growing environments such as temperature, light, fertility, soil pH, moisture and plant maturity levels, but without any change in the genotype. The following observations and size descriptions are based on a four-year-old plant growing in an outdoor full-sun trial garden and greenhouse forced two-year-old-plants at a wholesale perennial nursery in Zeeland, Mich. Plants were given supplemental water and fertilizer and plant growth regulators were used for the greenhouse trials only.

Botanical classification: *Salvia pratensis* (Linnaeus);

Parentage: Female or seed parent 'Pink Dawn'; unknown male or pollen parent;

Plant habit: Winter-hardy herbaceous perennial; multi-stemmed, compact, rounded, with mostly basal foliage, and flowers in several tightly arranged verticils on branched upright racemes displayed above foliage; in flower with panicles about 50 cm tall and about 45 cm wide at the fullest point; foliage extends up the stems about 22.5 cm and 45.0 cm wide below foliage;

Propagation: By basal vegetative shoot cuttings also in tissue culture and division; time to produce a rooted stems about two weeks;

Growth rate: Rapid, vigorous, finishing in a 65 mm container in about 7 weeks from rooted cutting, and from 65 mm container to flowering 3.8 liter container in about 8 weeks.

Root description: Fine, well-branched; color dependent on age and soil type, from cream to dark tan in color;

Foliage: Opposite, simple, rugose, lanceolate; margin crenulate; glabrous and matte abaxial and adaxial surfaces; acute apex and base cordate to auriculate with lobes frequently overlapping; leaf blades about 12.5 cm long and 5.2 cm across, decreasing in size distally; average about 9.8 cm long and 4.0 cm across; faint sage fragrance;

Foliage color: Adaxial surface nearest RHS 138A; abaxial surface nearest RHS 146B;

Venation: Reticulate; impressed on adaxial side and costate on abaxial side; pubescent abaxial, puberulent adaxial;

Vein color: Adaxial midrib variable, nearest RHS 157C; adaxial primary and secondary veins nearest RHS 157C toward midrib and gradually darkening to nearest RHS 138A toward margins; abaxial midrib nearest RHS 157C; abaxial primary and secondary veins nearest RHS 157C with secondary veins gradually becoming same color as leaf;

Petiole: Concavo-convex; pubescent abaxial and along margin, sparsely puberulent adaxial; to about 5.5 cm long and 4.0 mm wide, average 4.2 cm long and 3.5 mm wide at base;

Petiole color: Adaxial and abaxial margins nearest 137B with adaxial and abaxial center nearest RHS 157C;

Flower description: Perfect, bilabiate, verticillate with flowering generally beginning at lower verticils and advancing up the scape, but not all flowers at each verticil opening at the same time giving the effect of a scape being in continuous flower for longer periods; average distance between verticils about 14.0 mm, greater proximally and less distally; with center midline of flower about 15 degree angle above horizontal and hood petal about 50 degree angle above horizontal; self-cleaning, petals not persistent; flowering beginning late spring for about six weeks and repeating if initial scapes removed;

Flower longevity: About four days on the plant or as cut flower;

Fragrance: None detected under present growing conditions;

Flower buds one to two days prior to anthesis: Shape slightly arcuate, rounded on top and slightly concave below, with rounded apex; pubescent; about 11.0 mm long, 5.0 mm tall and 3.0 mm wide;

Bud color: Exposed petals between RHS 64D and RHS 64C; abaxial calyx nearest RHS 138A with veins and blushing on dorsal portion nearest RHS N77D;

Flowers: Bilabiate corolla with arcuate hooded upper lip and tri-lobed lower lip; about 2.4 cm long, 14.0 mm tall and 8.0 mm wide fused into tube in the proximal 8.0 mm; clustered at verticils with about six flowers per verticil;

Petals: Bilabiate corolla; upper hood petal and flattened side to side vertically, with notched apex and base fused with labium;

Hood (upper) petal: Minutely puberulent outside, glabrous inside; about 20.0 mm long, 10.0 mm tall and 3.0 mm across;

Labium (lower) petal: Consisting of three lobes, two proximal lobes about 3.0 mm long and 3.0 mm wide at base with rounded apex; center lobe emarginate, about 5.0 mm long 7.0 mm wide with a 2.0 mm apical notch in middle; center lobe slightly concaved upwards; total labium about 15.0 mm long, 8.0 mm wide at the widest portion across lobes and 5.0 mm tall;

Petal color: Abaxial and adaxial hood petal blend between RHS 75C and RHS 73D; lower labium petal abaxial near margin nearest RHS 75D, abaxial toward longitudinal center nearest RHS N78D, lower labium adaxial nearest RHS 75D toward margin and nearest RHS N78C toward longitudinal center; fused basal 2.0 mm inside calyx nearest RHS NN155D;

Androecium: Two, fused with labium, contained within hood petal except when triggered by pollinator;

*Filament*.—Glabrous, fused about 7.0 mm from base of labium petal; curved around inside of hood petal; about 12.5 mm long and less than 0.5 mm diameter with a 2.0 mm trip mechanism at base; color nearest RHS NN155D and in distal 2.0 mm region before stamen becoming nearest RHS 76C.

*Anther*.—Glabrous, oblong, about 3.0 mm long and 1.0 mm diameter; longitudinal, dorsifixed; color nearest RHS N187A.

*Pollen*.—Abundant; globose; less than 0.1 mm circumference; color nearest RHS 14A.

Gynoecium: One, curved around inside of hood petal;

*Style*.—About 24.0 mm long and less than 0.5 mm diameter; color nearest RHS NN155D and darkening distally about 3.0 mm before stigma split to nearest RHS 77B.

*Stigma*.—Bifurcate and curved in the terminal 2.0 mm; apex pointed; color nearest RHS 77B.

*Ovary*.—Superior; color more green than RHS 145A and more yellow than RHS 138B.

Fruit: Nutlet, one to four per flower; rounded, about 1.5 mm diameter; color darker than RHS 200A;

Calyx: Five sepals, three upper and two lower, campanulate, apex acute; fused in basal 4.0 mm; tube about 7.0 mm long and 6.0 mm tall at mouth and 3.0 mm wide; lower set bifurcate in terminal 2.5 mm; upper set of trifurcate in distal 1.0 mm;

Calyx color: Variable with light intensity, abaxial bases and regions in little direct sunlight nearest RHS 145A with veins of nearest RHS 138A, abaxial regions receiving more intense light developing tinting nearest RHS N77D; adaxial between RHS 146D and RHS 146C with darker veins of RHS 137A toward apex;

Bracts: Each verticil subtended by two opposite cordate to lanceolate bracts; apex narrowly acuminate, base truncate, margin entire and ciliolate; coarsely wavy to bent downward toward apex; margin minutely puberulent, and glabrous above and below; bract size up to 12.0 mm long and 7.0 mm wide, decreasing distally;

Bract color: Slightly variable with light intensity; in less light abaxial and adaxial surfaces nearest RHS 138A with midrib and base nearest RHS 145C; color with more intense light developing blushing nearest RHS N186C on both surfaces;

Peduncles: Raceme; quadrangular in base cross section; about 20 per plant; strong; upright; to about 50.0 cm tall and 5.0 mm across; puberulent to glandular; branches in lower two to four nodes, upright at 60 degrees above horizontal or greater; branches to about 24.0 cm long and 3.0 mm across; average internode distance about 5.0 cm;

Peduncle color: Between RHS 138A and RHS 138B;

Pedicels: Cylindrical; puberulent to glandular; about 1.5 mm long and 0.5 mm diameter; puberulent to glandular; nearly horizontal at flower anthesis;

Pedicel color: Variable with light intensity, ventral portion between RHS 146C and RHS 146D with lower light exposure; between RHS N186B and RHS N186C in dorsal portions with intense light;

Disease and pest resistance: Plants of *Salvia* 'Ballerina Pink' perform best with adequate moisture and good drainage and are hardy from USDA zone 3 to 8. Resistant to diseases and pests beyond that common to *Salvia* has not been noted.

It is claimed:

1. The new and distinct perennial *Salvia* plant named 'Ballerina Pink' as herein described and illustrated useful for landscaping as a specimen plant, en masse or as a cut flower.

* * * * *